United States Patent [19]

Bar-Or et al.

[11] Patent Number: 5,725,489
[45] Date of Patent: Mar. 10, 1998

[54] SPLINT STRUCTURE

[75] Inventors: Jonathan Bar-Or, Mobile Post Menashe; Roger H. Nathan, Herzlia; Harold Weingarden, Raanana, all of Israel

[73] Assignee: N.E.S.S. Neuromuscular Electrical Stimulation Systems Ltd., Raanana, Israel

[21] Appl. No.: 540,819

[22] Filed: Oct. 11, 1995

[30] Foreign Application Priority Data

Oct. 12, 1994 [IL] Israel ................... 111264

[51] Int. Cl.$^6$ ................... A61F 5/00; A61F 5/01
[52] U.S. Cl. ................... 602/21; 602/20; 602/6; 602/16
[58] Field of Search ................... 2/2, 16; 602/5, 602/16, 20, 21, 23, 27, 61, 64, 19, 26, 12; 623/62, 33, 57, 61

[56] References Cited

U.S. PATENT DOCUMENTS

| | | | |
|---|---|---|---|
| 315,512 | 4/1885 | Kearns | 602/21 |
| 323,775 | 8/1885 | Blender et al. | 602/12 |
| 1,257,297 | 2/1918 | Brown | 602/16 |
| 2,318,864 | 5/1943 | Jackson | 602/21 |
| 2,943,622 | 7/1960 | Nelson | 602/16 |
| 3,792,537 | 2/1974 | Plank et al. | 36/87 |
| 4,256,097 | 3/1981 | Willis | 602/16 |
| 4,465,064 | 8/1984 | Boone | 602/16 X |
| 4,768,502 | 9/1988 | Lee | 602/20 X |
| 4,950,273 | 8/1990 | Briggs | 606/113 |
| 5,197,943 | 3/1993 | Link | 602/5 |
| 5,348,530 | 9/1994 | Grim et al. | 602/12 X |
| 5,441,015 | 8/1995 | Farley | 602/27 X |
| 5,509,426 | 4/1996 | Sowerby | 128/878 |

*Primary Examiner*—Richard J. Apley
*Assistant Examiner*—Denise Pothier
*Attorney, Agent, or Firm*—Jacobson, Price, Holman & Stern, PLLC

[57] ABSTRACT

A crocodile-type splint, including a first jaw having a substantially trough-like structure at least approximately conforming to sections of the palmar side of a limb, a second jaw having a substantially trough-like structure at least approximately conforming to sections of the dorsal side of the limb, a first joint whereby the jaws are articulated to one another to the effect of permitting the trough-like jaws to include with one another a range of different angles, from an angle small enough for the jaws to clampingly surround the limb, to an angle large enough to at least permit the limb to be freely introduced between the two jaws.

6 Claims, 4 Drawing Sheets

SPLINT STRUCTURE

The present invention relates to a splint structure, in particular to a crocodile-type splint to fit on a body limb such as a forearm. The invention is also concerned with a mechanism for controlling the relative positions of the two splint halves over a defined angular range.

The disadvantage of such exoskeletal devices as splints largely resides in the fact that, for the average handicapped person, they are very difficult, if not impossible, to don and doff without assistance and thus, to some degree at least, impair their sense of independence that is otherwise enhanced by these devices.

It is thus one of the objects of the present invention to provide a splint that can be easily donned and doffed by a person with a minimum of residual hand function in the active hand and that stays properly seated during arm and hand movements without either uncontrolledly slipping about, or else impairing muscular function due to a rigid fit that does not allow for necessary changes in the effective thickness of the forearm, e.g., during pronation-supination.

According to the invention, the above object is achieved by providing a crocodile-type splint comprising a first jaw having a substantially trough-like structure at least approximately conforming to sections of the palmar side of a limb; a second jaw having a substantially trough-like structure at least approximately conforming to sections of the dorsal side of said limb; a first joint whereby said jaws are articulated to one another to the effect of permitting said trough-like jaws to include with one another a range of different angles, from an angle small enough for said jaws to clampingly surround said limb, to an angle large enough to at least permit said limb to be freely introduced between said two jaws.

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Figure 1:
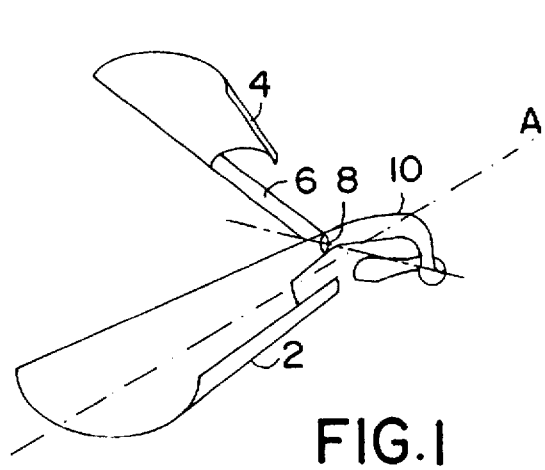
FIG. 1 is a perspective schematic representation of a crocodile splint without the controlling mechanism.

Referring now to the drawings, there is seen in FIG. 1 a schematically illustrated basic crocodile splint comprising a lower jaw 2 and an upper jaw 4 which, by means of an arm 6 and a pivot 8, are articulated to one another. Advantageously, the lower jaw is provided with a loop-like extension 10 that encompasses a portion of the wearer's hand. The axis of pivot 8 extends in a direction perpendicular to the longitudinal axis A of the splint. The mechanism facilitating control of the relative positions of the lower jaw 2 and the upper jaw 4 is described further below.

Figure 2:
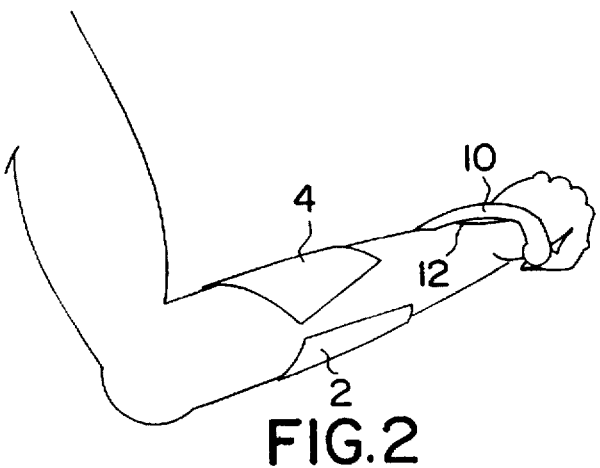
FIG. 2 shows the splint as mounted on the forearm of a user.

FIG. 2 shows the splint according to the invention as fitted on the forearm of a patient. An important element in the good fit of the splint is a pad 12 inserted into, and filling, whatever clearance there is left between the upper, bow-like portion of the extension 10 and the back of the hand. This is especially advantageous if the splint contains stimulating or monitoring electrodes, as the pad 12 lowers the palmar surface of the forearm and aligns it with the lower surface of the splint, thus ensuring positive contact of the forearm surface with the electrodes. These pads can be manufactured in a number of sizes or thicknesses, thereby reducing the number of different splint sizes required for proper fitting, as the same splint size may be adapted to fit different forearms by the use of appropriate pads 12.

Figure 3:
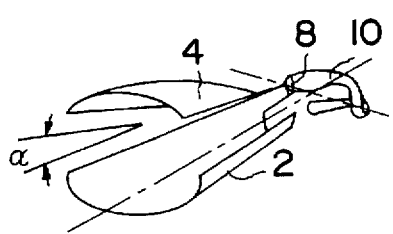
FIGS. 3 to 6 show different stages in the opening of the splint jaws.

FIG. 3 shows the jaws 2 and 4 of the crocodile splint in the fully closed position at an angle $\alpha$ of approximately 10°, at which they fit intimately onto the palmar and dorsal surfaces of a thin or atrophied forearm.

Figure 4:
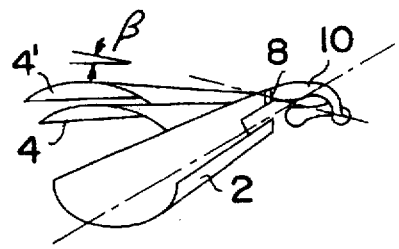

FIG. 4 shows that in the fully closed position of FIG. 3, flexibility due to elastic deformation of a part of the ratchet mechanism (to be explained further below) permits an additional rotation of the upper jaw from position 4 to position 4' of an angle $\beta=4°$, at a spring constant of about 10' Nm/radian. This feature results in a fairly even pressure between the splint jaws and electrodes and the forearm surface, maintained also during articulation of the limb when the effective thickness of the forearm may change.

Figure 5:
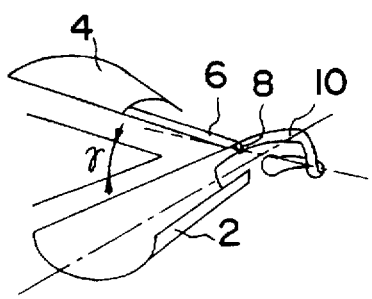

Up to an angle of $\tau$ (FIG. 5), the already-mentioned pawl-and-ratchet mechanism is effective to permit the upper jaw 4 to be tightly closed down onto the forearm, in which position it is locked by the ratchet mechanism, until manually released in a manner to be explained. A wide range of limb sizes can be housed between the two extreme positions, angles $\alpha$ and $\tau$. The flexibilty mentioned in conjunction with FIG. 4 is effective at whatever angular position in which jaw 4 is locked.

Beyond the angle $\tau$ and up to an angle of $\delta$, the upper jaw 4 is prevented from falling back to the closed position under the effect of gravity by controlled friction produced by a detent element, which is part of the mechanism to be explained presently.

Figure 7:
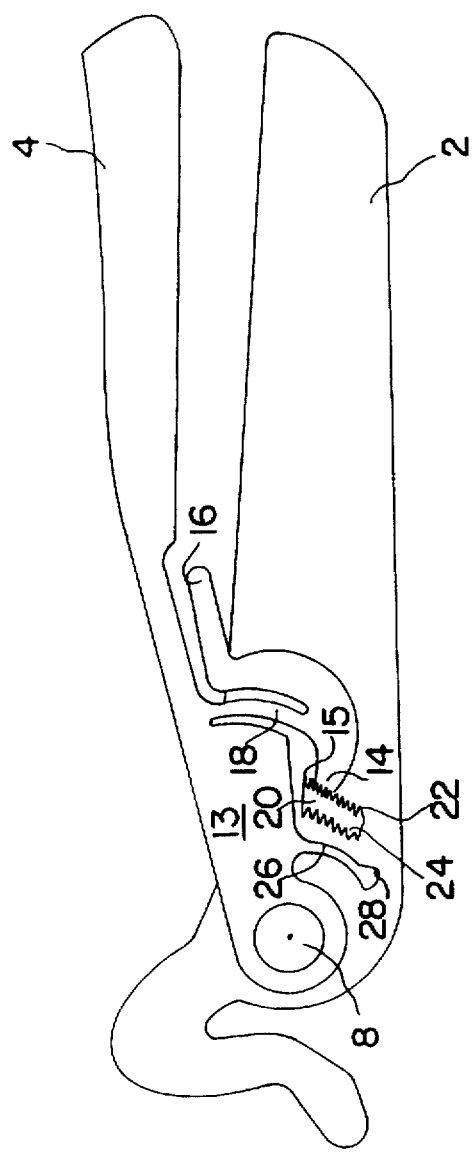
FIG. 7 is a schematic drawing of the pawl-and-ratchet mechanism that controls the relative positions of the splint jaws.

FIG. 7 is a schematic representation of the pawl-and-ratchet mechanism that controls the relative positions of the splint jaws 2, 4.

The lower jaw 2 and upper jaw 4 are articulated to one another by means of a pivot 8. The ratchet mechanism is substantially planar and comprises a flat base plate 13 fixedly attached to the upper jaw 4. With this plate 13 are advantageously integral a pawl 14 with one or several teeth 15, a release lever 16 and a cantilever spring 18. Further seen is a ratchet segment 20 which, in co-planar relationship with the base plate 13, is fixedly connected to the lower jaw 2 and carries on one side a set of downwardly-pointing, relatively fine and sharp saw teeth 22 and, on the other side, a set of upwardly-pointing, relatively coarse and dull saw teeth 24.

The cantilever spring 18 biases the pawl 14 against the ratchet segment 20.

Also seen is an additional cantilever spring 26 connected to the upper jaw 4 and having a nose 28. The function of spring 26 will be explained further below.

Figure 8:
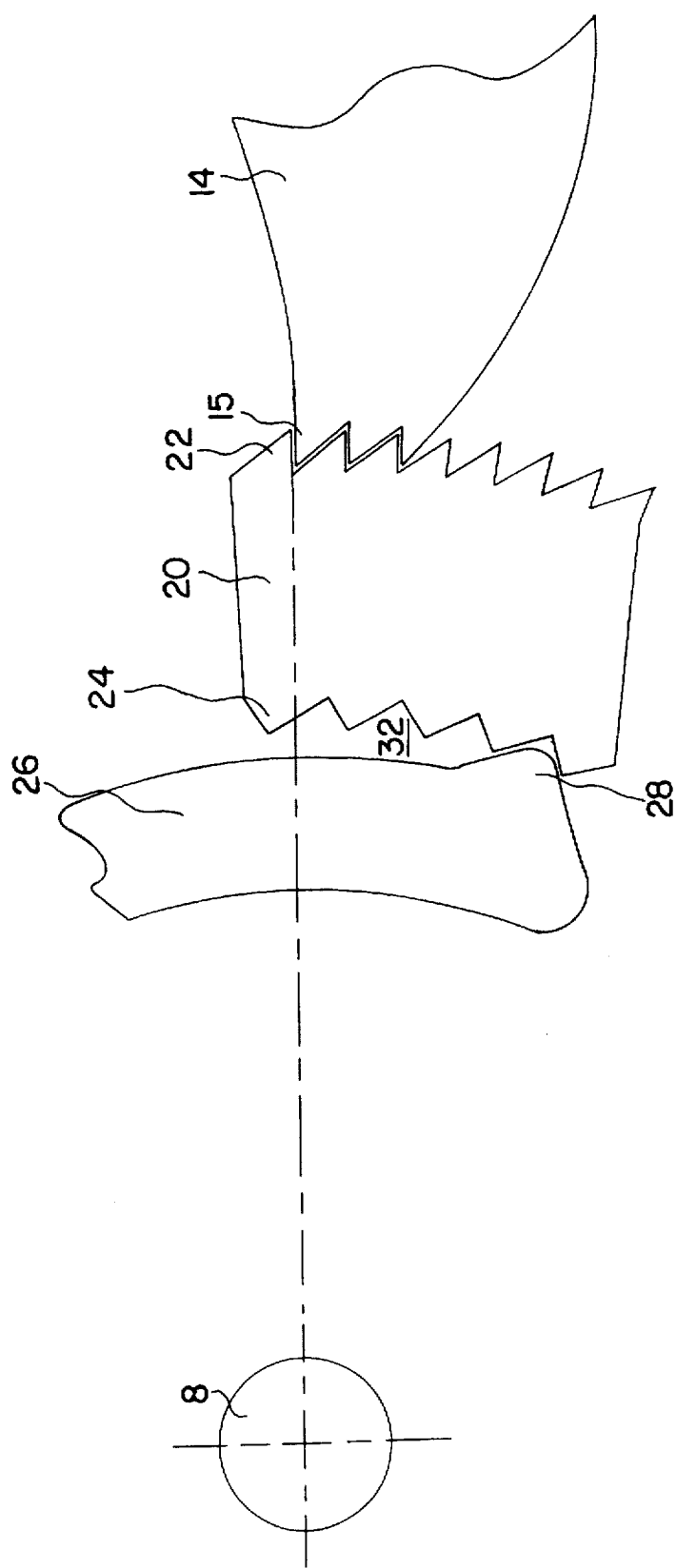
FIG. 8 is an enlarged drawing of the elements of the pawl-and-ratchet mechanism.

The active members of the pawl-and-ratchet mechanism are shown to an enlarged scale in FIG. 8, showing the various tooth shapes. When a torque about pivot 8 is applied tending to separate the splint jaws 2 and 4, the upper surfaces of teeth 15 and the lower surfaces of teeth 22 engage, thus effectively locking the splint in its instantaneous position.

Opening the jaws 2, 4 is effected by pushing the release lever 16 in the upwards direction, which, overcoming the biasing force of the cantilever spring 18, flexes the latter at about the upper end thereof, thereby disengaging the pawl teeth 15 from the ratchet teeth 22. By continuing to pull the release lever 16, the latter abuts against the edge of the upper jaw 4 and drags the jaw 4 along.

Closing of the splint is effected by pushing the upper jaw 4 downwards against the lower jaw 2. Now the torque produced about the pivot 8 acts in the opposite direction; the slanting faces of the respective sets of teeth 15, 22 slide along one another against the biasing force of the cantilever spring 18, while producing the characteristic clicking sound of a ratchet. This arrangement thus forms what is essentially a one-way ratchet mechanism.

Another feature of the mechanism already referred to in conjunction with FIG. 4 is its springiness over an angle β. In the embodiment shown, this feature is achieved by the curved shape of the cantilever spring 18. When the splint is worn on a forearm, a force is present tending to push apart the jaws 2, 4, due to the resilience of the soft tissues of the limb under compression. With the ratchet mechanism locked, the above-mentioned "give" of about 4° is due to the curved cantilever spring 18 straightening out in response to the forces between jaws 2 and 4.

Figure 9:
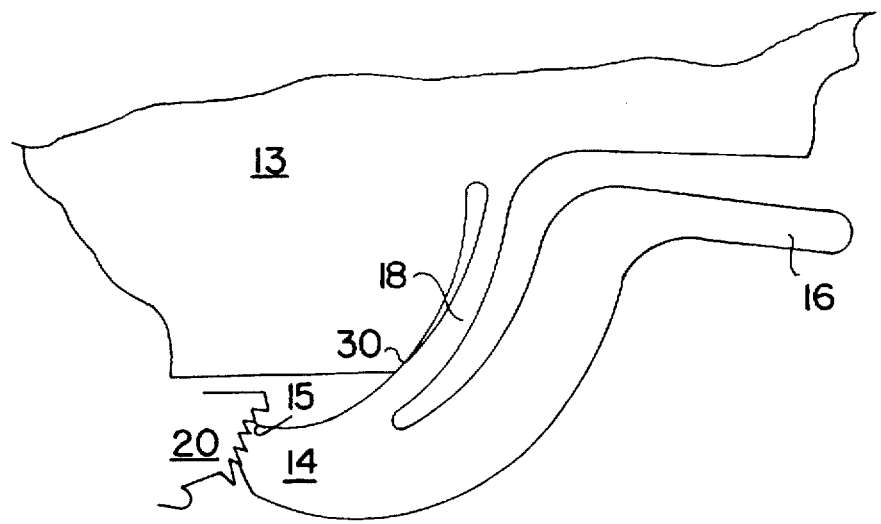
FIG. 9 illustrates the workings of a mechanical safety arrangement protecting the ratchet mechanism against overloading.

The above-described mechanism also incorporates an overload safety feature which comes into action when excessive force is applied to separate jaws 2 and 4, for instance, when the upper jaw 4 is pulled upward without releasing the pawl 14. In such a case, illustrated in FIG. 9, the cantilever spring 18 flexes and straightens until it makes contact with the edge 30 of the base plate 13. From this moment on, a further pull at the upper jaw 4 will cause the pawl teeth 15 to swing about the edge 30 in a counter-clockwise direction, resulting in an eventual disengagement of pawl 14 and ratchet 20, and a restoration, without mechanical damage, of the original configuration.

Figure 6:
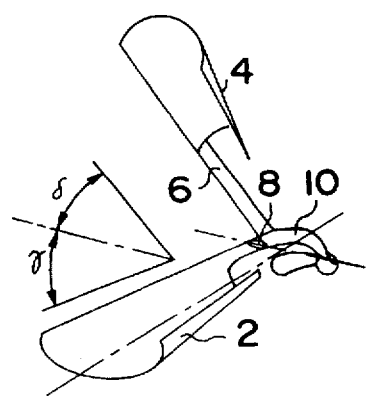

Beyond the angle τ and over the angle δ in FIG. 6, the above-discussed locking mechanism is no longer active, as at that angle, the last pawl tooth 15 will have left the last ratchet tooth 22. At this point, another mechanism takes over, which has no locking function but merely provides controlled friction, to at least hold up the upper jaw 4 against gravity, as shown in FIG. 6.

This is a detent arrangement comprising a set of comparatively dull teeth 24 opposite the set of ratchet teeth 15, producing between them detent notches 32 (FIG. 8), into which drops the nose 28 of the second cantilever spring 26 and from which it has to be lifted by the friction-producing relative movement between the spring-loaded nose 28 and the flanks of teeth 24. The friction produced depends on such parameters as the spring constant of the spring 26, the angle of the notches 32, the radius of the nose 28 and the coefficient of friction of the friction partners. It wall also be appreciated that, due to the non-symmetry of the notches 32 (see FIG. 8), a greater force is required to overcome friction in the direction of closure of the jaws 2, 4 than in the direction of opening.

Other arrangements of this ratchet and friction mechanism are also feasible, such as arranging the interacting teeth on either or both the friction and the ratchet members of the mechanism to operate in a plane perpendicular to the direction shown in FIG. 7. This would, however, be less compact an arrangement. A friction mechanism could also be used similar to the brakes or clutch assembly on a motor vehicle.

It should be understood that the splint according to the invention can also be used in its basic form as shown in FIG. 1, without the locking mechanism, other means being used to attach the crocodile splint to the user's limb.

Figure 10:
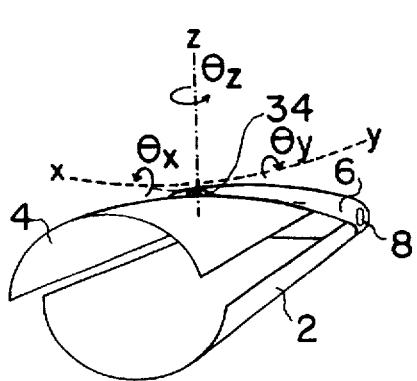
FIG. 10 shows an arrangement ensuring self-alignment between upper and lower jaws.

A variant of the crocodile splint described is seen in FIG. 10, which ensures full self-alignment of the two jaws 2, 4, and thus a better fit. In this variant, the arm 6 of FIG. 1 by which the upper jaw 4 is articulated to the lower jaw 2 (i.e., to an extension 10 thereof) is not integral with, or fixedly attached to, the upper jaw 4, but is articulated to the latter by a joint 34 permitting it three degrees of freedom in rotation relative to the lower jaw 2, i.e., rotation $\Theta_x$ about an x-axis, rotation $\Theta_y$ about a y-axis, and rotation $\Theta_z$ about a vertical z-axis. The joint 34 is thus a ball joint or the kinematic equivalent of a ball joint.

Clearly, a force such as the spring force supplied by the pawl-and-ratchet arrangement explained above, or any other force used to press the two jaws 2, 4 together, will always cause the two jaws to arrange themselves in perfect alignment.

Figure 11:
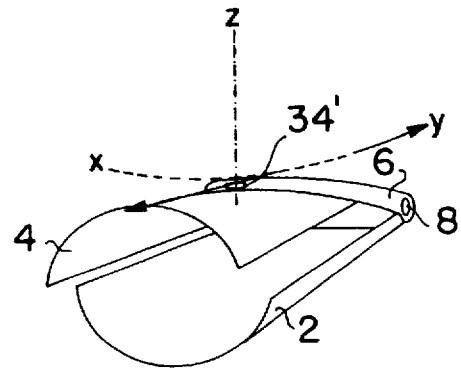
FIG. 11 is a similar arrangement providing the upper jaw with an additional freedom of movement in translation.

In a further variant, the joint 34' is designed to provide the upper jaw 4 with an additional freedom of movement in translation along the y-axis of the forearm, as shown in FIG. 11. This feature can be utilized to minimize the actual surface area or coverage of the upper jaw 4 on the forearm for the function required of it (e.g., holding electrodes onto the skin surface), while allowing the jaw to be moved backwards or forwards to allow for variations in arm length.

It will be evident to those skilled in the art that the invention is not limited to the details of the foregoing illustrated embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A forearm-hand splint for use by a handicapped person, comprising:

a first elongate jaw having a wrist end and a substantially straight and continuous, concave structure at least approximately conforming to sections of the palmar side of a limb;

a second elongate jaw having a wrist end and a substantially straight and continuous, concave structure at least approximately conforming to sections of the dorsal side of said limb;

the first jaw and the second jaw defining an opening at the wrist end of each of the jaws for passage therethrough of the limb of a person, a first joint between the jaws, located adjacent to the wrist end of the first jaw and the second jaw, including pivot means having an axis which extends in a direction perpendicular to the longitudinal extent of said jaws so that said jaws are articulated to one another to the effect of permitting said jaws to include with one another a range of different angles, from an angle small enough for said jaws to clampingly surround said limb, to an angle large enough to at least permit said limb to be freely introduced between said two jaws to be easily donned and doffed by a person with a minimum of residual hand function in the limb to which the splint is to be applied.

2. The splint as claimed in claim 1, further comprising an extension of said first jaw that loops around a portion of the wearer's hand.

3. The splint as claimed in claim 1, further comprising a pawl-and-ratchet mechanism, including:

a toothed pawl carrying on one of its ends a release lever and being attached to a first end of a first cantilever spring, the second end of which is attached to said second jaw, said first end of said first cantilever spring being adapted to act on said pawl;

a toothed ratchet member fixedly attached to a section of said first jaw and, for at least a first part of said angular range, being capable of engagement with said pawl under the biasing effect of said cantilever spring on said pawl, whereby said mechanism will permit said two jaws to approach one another, but will cause said pawl to engage said ratchet and prevent movement of said jaws when a force is applied to separate said jaws without activating said release lever.

4. The splint as claimed in claim 3, further comprising a second cantilever spring at least indirectly attached with one of its ends to said second jaw, the second end of which spring is in the form of a nose adapted to interact with a sequence of detent notches provided in a member fixedly attached to a section of said first jaw, whereby, over a second part of said angular range, the friction provided by the interaction of said nose and said notches prevents said large enough angle to be reduced by the force of gravity.

5. The splint as claimed in clam 1, further comprising a second joint by means of which said second jaw is connected to said first joint, said second joint conferring upon said second jaw three degrees of freedom of movement in rotation.

6. The splint as claimed in claim 5, wherein said second joint also confers upon said second jaw one degree of freedom of movement in translation.

* * * * *